US008571687B2

(12) United States Patent
Libbus et al.

(10) Patent No.: US 8,571,687 B2
(45) Date of Patent: Oct. 29, 2013

(54) TRANSCUTANEOUS NEUROSTIMULATOR FOR MODULATING CARDIOVASCULAR FUNCTION

(75) Inventors: Imad Libbus, St. Paul, MN (US); Anthony V. Caparso, San Jose, CA (US); Andrew P. Kramer, Marine on St. Croix, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/869,593

(22) Filed: Aug. 26, 2010

(65) Prior Publication Data
US 2010/0324621 A1 Dec. 23, 2010

Related U.S. Application Data

(63) Continuation of application No. 11/548,359, filed on Oct. 11, 2006, now Pat. No. 7,797,041.

(51) Int. Cl.
*A61N 1/18* (2006.01)

(52) U.S. Cl.
USPC .................. 607/149; 607/2; 607/9; 607/44

(58) Field of Classification Search
USPC ......... 607/2, 30–33, 36, 37, 59, 60, 142, 145, 607/149; 128/903, 907; 600/523
See application file for complete search history.

(56) References Cited

U.S. PATENT DOCUMENTS

| | | |
|---|---|---|
| 3,650,277 A | 3/1972 | Sjostrand et al. |
| 3,938,526 A | 2/1976 | Anderson |
| 4,690,144 A | 9/1987 | Rise et al. |
| 4,712,558 A | 12/1987 | Kidd et al. |
| 5,193,539 A | 3/1993 | Schulman et al. |
| 5,211,175 A | 5/1993 | Gleason et al. |
| 5,335,657 A | 8/1994 | Terry, Jr. et al. |
| 5,487,759 A | 1/1996 | Bastyr et al. |
| 5,540,734 A | 7/1996 | Zabara |
| 5,571,150 A | 11/1996 | Wernicke et al. |
| 5,707,400 A | 1/1998 | Terry, Jr. et al. |

(Continued)

FOREIGN PATENT DOCUMENTS

| | | |
|---|---|---|
| AU | 2007308099 | 1/2012 |
| EP | 1078649 | 2/2001 |

(Continued)

OTHER PUBLICATIONS

"Australian Application Serial No. 2007308099, Request to Amend a Complete Specification and Second Statement of Proposed Amendments filed Jul. 13, 2011 in Response to First Examiner Report dated Oct. 1. 2010", 19 pgs.

(Continued)

*Primary Examiner* — Allen Porter, Jr.
(74) *Attorney, Agent, or Firm* — Schwegman Lundberg & Woessner, P.A.

(57) ABSTRACT

A neurostimulation device includes an external neurostimulator worn by a patient using a bracing element that braces a portion of the patient's body. The external neurostimulator delivers neurostimulation to modulate a cardiovascular function of the patient. In one embodiment, the external stimulator delivers the neurostimulation transcutaneously to a stimulation target in the patient's body using surface stimulation electrodes placed on the body approximately over the stimulation target.

17 Claims, 12 Drawing Sheets

(56) References Cited

U.S. PATENT DOCUMENTS

| | | | |
|---|---|---|---|
| 6,057,758 A | 5/2000 | Dempsey et al. | |
| 6,106,477 A | 8/2000 | Miesel et al. | |
| 6,169,924 B1 | 1/2001 | Meloy et al. | |
| 6,208,902 B1 | 3/2001 | Boveja | |
| 6,246,912 B1 | 6/2001 | Sluijter et al. | |
| 6,269,270 B1 | 7/2001 | Boveja | |
| 6,393,325 B1* | 5/2002 | Mann et al. | 607/46 |
| 6,449,507 B1 | 9/2002 | Hill et al. | |
| 6,493,592 B1 | 12/2002 | Leonard et al. | |
| 6,522,927 B1 | 2/2003 | Bishay et al. | |
| 6,539,264 B1 | 3/2003 | Bishay et al. | |
| 6,556,869 B1 | 4/2003 | Leonard et al. | |
| 6,615,085 B1 | 9/2003 | Boveja | |
| 6,622,047 B2 | 9/2003 | Barrett et al. | |
| 6,658,298 B2 | 12/2003 | Gruzdowich et al. | |
| 7,089,061 B2 | 8/2006 | Grey | |
| 7,191,012 B2 | 3/2007 | Boveja et al. | |
| 7,263,405 B2 | 8/2007 | Boveja et al. | |
| 7,308,318 B2 | 12/2007 | Miazga et al. | |
| 7,321,792 B1 | 1/2008 | Min et al. | |
| 7,376,467 B2 | 5/2008 | Thrope et al. | |
| 7,403,821 B2 | 7/2008 | Haugland et al. | |
| 7,797,041 B2 | 9/2010 | Libbus et al. | |
| 7,797,046 B2 | 9/2010 | Libbus et al. | |
| 8,396,556 B2 | 3/2013 | Libbus et al. | |
| 2001/0034544 A1 | 10/2001 | Mo | |
| 2002/0040234 A1 | 4/2002 | Linberg | |
| 2002/0133210 A1 | 9/2002 | Gruzdowich et al. | |
| 2002/0143369 A1 | 10/2002 | Hill et al. | |
| 2002/0183799 A1 | 12/2002 | Silvian | |
| 2002/0183804 A1* | 12/2002 | Malaney et al. | 607/48 |
| 2003/0014088 A1* | 1/2003 | Fang et al. | 607/48 |
| 2003/0093127 A1 | 5/2003 | Dalal | |
| 2003/0144710 A1* | 7/2003 | Haugland et al. | 607/48 |
| 2003/0191504 A1 | 10/2003 | Meadows et al. | |
| 2003/0195585 A1 | 10/2003 | Gruzdowich et al. | |
| 2004/0015081 A1 | 1/2004 | Kramer et al. | |
| 2004/0034394 A1* | 2/2004 | Woods et al. | 607/46 |
| 2004/0063456 A1 | 4/2004 | Griffin et al. | |
| 2004/0102818 A1 | 5/2004 | Hakky et al. | |
| 2004/0147996 A1 | 7/2004 | Miazga et al. | |
| 2004/0172096 A1 | 9/2004 | Giuntoli et al. | |
| 2004/0210261 A1 | 10/2004 | King et al. | |
| 2004/0236387 A1* | 11/2004 | Fang et al. | 607/48 |
| 2005/0107841 A1* | 5/2005 | Meadows et al. | 607/43 |
| 2005/0192644 A1 | 9/2005 | Boveja et al. | |
| 2005/0277844 A1 | 12/2005 | Strother et al. | |
| 2005/0278000 A1 | 12/2005 | Strother et al. | |
| 2005/0283202 A1 | 12/2005 | Gellman | |
| 2006/0004423 A1 | 1/2006 | Boveja et al. | |
| 2006/0095081 A1 | 5/2006 | Zhou et al. | |
| 2006/0122675 A1 | 6/2006 | Libbus et al. | |
| 2006/0178660 A1 | 8/2006 | Neher et al. | |
| 2006/0178661 A1 | 8/2006 | Neher et al. | |
| 2006/0206163 A1 | 9/2006 | Wahlstrand et al. | |
| 2006/0293712 A1 | 12/2006 | Kieval et al. | |
| 2007/0067000 A1 | 3/2007 | Strother et al. | |
| 2007/0162090 A1 | 7/2007 | Penner | |
| 2007/0265674 A1 | 11/2007 | Olson et al. | |
| 2008/0091248 A1 | 4/2008 | Libbus et al. | |
| 2008/0091256 A1 | 4/2008 | Libbus et al. | |
| 2010/0324620 A1 | 12/2010 | Libbus et al. | |
| 2011/0082515 A1 | 4/2011 | Libbus et al. | |

FOREIGN PATENT DOCUMENTS

| | | |
|---|---|---|
| EP | 1078649 A1 | 2/2001 |
| JP | 5010683 | 6/2012 |
| JP | 5011392 | 6/2012 |
| WO | WO-0103768 A1 | 1/2001 |
| WO | WO-2008045597 A1 | 4/2008 |
| WO | WO-2008045598 A1 | 4/2008 |

OTHER PUBLICATIONS

"European Application Serial No. 07798601.6, Response filed Jul. 6, 2011 to Office Action dated Mar. 10, 2011,", 8 pgs.

"Australian Application Serial No. 2007308099, First Examiner Report mailed Oct. 1, 2010", 2 Pgs.

"European Application Serial No. 07798601.6, Office Action mailed Mar. 10, 2011", 5 pgs.

"European Application Serial No. 07798601.6, Response filed May 28, 2010 to Office Action mailed Feb. 5, 2010", 18 pgs.

"European Application Serial No. 07798604.0, Response filed Mar. 26, 2010 to Office Action mailed Sep. 29, 2009", 15 pgs.

"U.S. Appl. No. 11/548,348, Response filed Jan. 6. 2009 to Non Final Final Office Action mailed Oct. 7, 2008", 12 pgs.

"U.S. Appl. No. 11/548,348 Non-Final Office Action mailed Oct. 7, 2008", OARN, 19 pgs.

"U.S. Appl. No. 11/548,348 , Non-Final Office Action mailed Oct. 21, 2009", 15 Pgs.

"U.S. Appl. No. 11/548,348, Advisory Action mailed Aug. 7, 2009", 6 pgs.

"U.S. Appl. No. 11/548,348, Final Office Action mailed Apr. 23, 2009", 18 pgs.

"U.S. Appl. No. 11/548,348, Notice of Allowance mailed May 10, 2010", 14 pages.

"U.S. Appl. No. 11/548,348, Response filed Jul. 23, 2009 to Final Office Action mailed Apr. 23, 2009", 13 pgs.

"U.S. Appl. No. 11/548,348, Response filed Sep. 23, 2009 to Advisory Action mailed Aug. 7, 2009", 14 pgs.

"U.S. Appl. No. 11/548,348, Response filed Feb. 18, 2010 to Non Final Office Action mailed Oct. 21, 2009", 15 pgs.

"U.S. Appl. No. 11/548,359, Response filed Feb. 20, 2009 to Non-Final Office Action mailed Oct. 20, 2008", 16 pages.

"U.S. Appl. No. 11/548,359, Final Office Action mailed Jun. 24, 2009", 16 pgs.

"U.S. Appl. No. 11/548,359, Non-Final Office Action mailed Dec. 14, 2009", 20 pgs.

"U.S. Appl. No. 11/548,359, Notice of Allowance mailed May 12, 2010", 8 Pages.

"U.S. Appl. No. 11/548,359, Response filed Mar. 15, 2010 to Non Final Office Action mailed Dec. 14, 2009", 18 pgs.

"U.S. Appl. No. 11/548,359, Response filed Sep. 24, 2009 to Final Office Action mailed Jun. 24, 2009", 15 pgs.

"Application Serial No. 07798604.0, Office Action Mailed Nov. 27, 2009", 4 pgs.

"U.S. Appl. No. 11/548,359,Non-Final Office Action Mailed Oct. 20, 2008", 14 pgs.

"European Application Serial No. 07798601.6, Office Action Mailed Feb. 5, 2010", 3 Pages.

"PCT Application No. PCT/US2007/071283, International Search Report mailed Oct. 24, 2007", 5 pgs.

"PCT Application No. PCT/US2007/071283, Written Opinion mailed Oct. 24, 2007", 8 pgs.

"PCT Application No. PCT/US2007/071288, International Search Report mailed Dec. 4, 2007", 4 pgs.

"PCT Application No. PCT/US2007/071288, Written Opinion mailed Dec. 4, 2007", 7 pgs.

Caparso, A. V., et al., "Implantable Neurostimulator for Modulating Cardiovascular Function", U.S. Appl. No. 11/548,354, filed Oct. 11, 2006, 36 pgs.

Michikami, D., et al., "Short-term electroacupuncture at Zusanli resets the arterial baroreflex neural arc toward lower sympathetic nerve activity", Am J Physiol Heart Circ Physiol., [Epub ahead of print] doi: 10.1152/ajpheart.00975.2005, (Feb 24, 2006), 39 pgs.

Zhou, X, et al., "Prevention of high incidence of neurally mediated ventricular arrhythmias by afferent nerve stimulation in dogs", Circulation, 101(7), (Feb. 22, 2000), 819-24.

Zhou, X., et al., "Effects of peroneal nerve stimulation on hypothalamic stimulation-induced ventricular arrhythmias in rabbits", Am J Physiol. 267(5 Pt 2), (Nov. 1994), H2032-H2041.

"U.S. Appl. No. 12/869,579, Non Final Office Action mailed Dec. 22, 2011", 16pgs.

"U.S. Appl. No. 12/869,579, Examiner Interview Summary mailed Apr. 23, 2012", 3 pgs.

(56) References Cited

OTHER PUBLICATIONS

"U.S. Appl. No. 12/869,579, Final Office Action mailed Jul. 13, 2012", 17 pgs.
"U.S. Appl. No. 12/869,579, Response filed Apr. 17, 2012 to Non Final Office Action mailed Dec. 22, 2011", 14 pgs.
"U.S. Appl. No. 12/969,023, Non Final Office Action mailed Apr. 20, 2012", 14 pgs.
"European Application Serial No. 07798601.6, Office Action mailed Apr. 24, 2012", 5 pgs.
"European Application Serial No. 11190036.1, European Search Report mailed Mar. 30, 2012", 3 pgs.
"European Application Serial No. 11190036.1, Office Actin mailed Apr. 17, 2012", 5 pgs.
"European Application Serial No. 12153741.9, Office Action mailed May 14, 2012", 5 pgs.
"European Application Serial No. 12153741.9, Supplemental Search Report mailed Apr. 25, 2012", 3 pgs.
Yin Yang House.Web. Apr. 14, 2012, ""HT 7 Acupuncture Point—Shen Men—Heart Meridian" Yin Yang House.Web. Apr. 14, 2012. <http://www.yinyanghouse.com/acupuncturepoints/ht7>", 2 pgs.
"U.S. Appl. No. 12/869,579, Response filed Nov. 7, 2012 to Final Office Action mailed Jul. 13, 2013 and Advisory Action mailed Oct. 5, 2012", 14 pgs.
"U.S. Appl. No. 12/869,579, Advisory Action mailed Oct. 5, 2012", 5 pgs.
"U.S. Appl. No. 12/869,579, Non Final Office Action mailed Dec. 6, 2012", 20 pgs.
"U.S. Appl. No. 12/869,579, Response filed Sep. 13, 2013 to Final Office Action mailed Jul. 13, 2012", 14 pgs.
"U.S. Appl. No. 12/969,023, Notice of Allowance mailed Nov. 8, 2012", 8 pgs.
"U.S. Appl. No. 12/969,023, Response filed Aug. 16, 2012 to Non Final Office Action mailed Apr. 20, 2012", 11 pgs.
"European Application Serial No. 12153741.9, Response filed Sep. 17, 2012 to Office Action mailed May 14, 2012", 5 pgs.
"European Application Serial No. 07798601.6, Response filed Aug. 21, 2012 to Examination Notification Art. 94(3) mailed Apr. 24, 2012", 11 pgs.
"European Application Serial No. 11190036.1, Response filed Aug. 22, 2012 to Examination Notification Art. 94(3) mailed Apr. 17, 2012", 15 pgs.
"U.S. Appl. No. 12/869,579, Response filed Feb. 19, 2013 to Non Final Office Action mailed Dec. 6, 2012", 14 pgs.
"U.S. Appl. No. 12/869,579, Final Office Action mailed Apr. 16, 2013", 22 pgs.

* cited by examiner

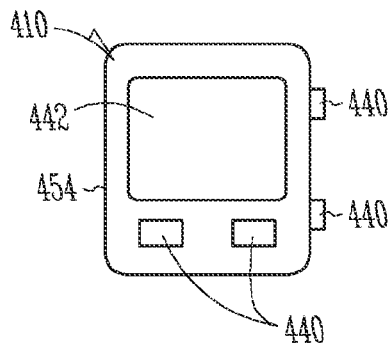
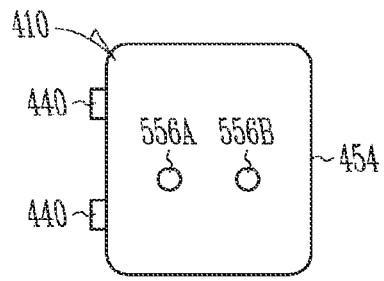
Fig. 4  Fig. 5
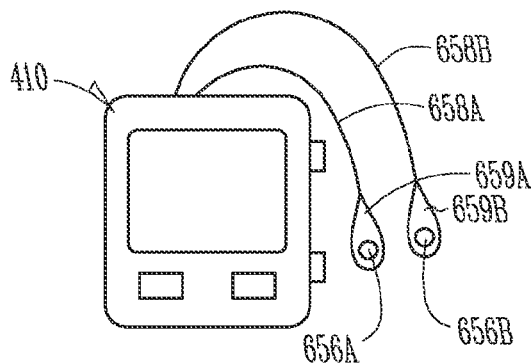
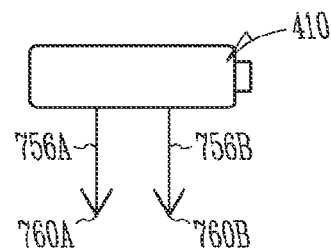
Fig. 6  Fig. 7
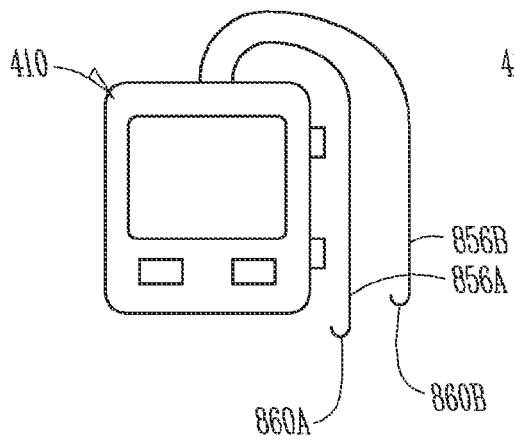
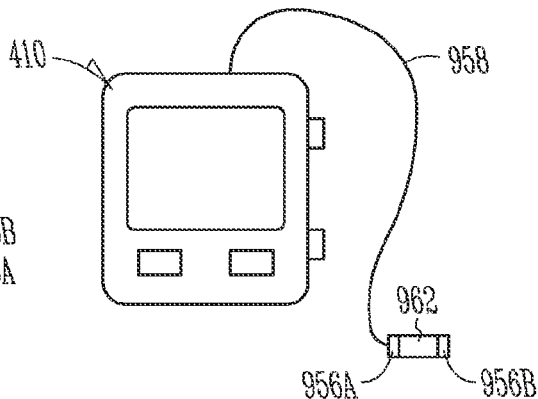
Fig. 8  Fig. 9

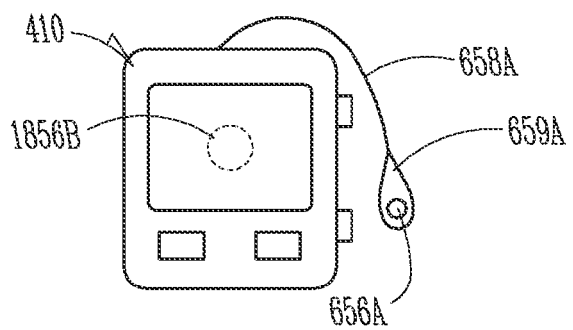
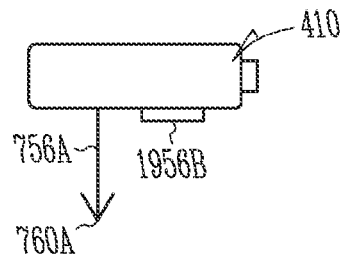
Fig.18  Fig.19
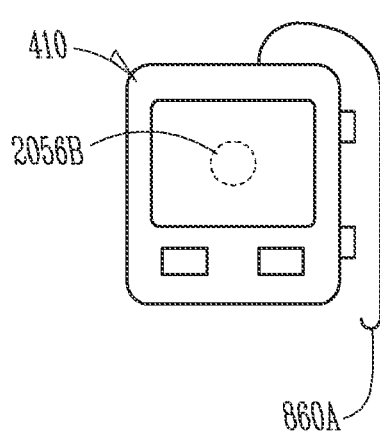
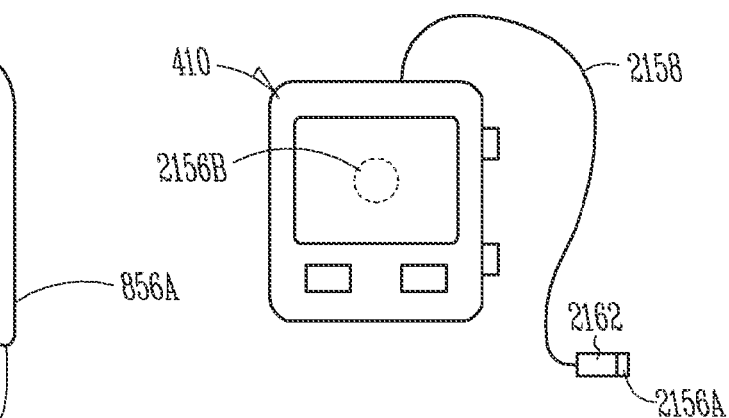
Fig.20  Fig.21

TRANSCUTANEOUS NEUROSTIMULATOR FOR MODULATING CARDIOVASCULAR FUNCTION

CLAIM OF PRIORITY

This application is a continuation of and claims the benefit of priority under 35 U.S.C. §120 to U.S. patent application Ser. No. 11/548,359, filed on Oct. 11, 2006, now issued as U.S. Pat. No. 7,797,041, which is hereby incorporated by reference herein in its entirety.

CROSS-REFERENCE TO RELATED APPLICATION

This application is related to co-pending, commonly assigned, U.S. patent application Ser. No. 11/548,348, entitled "PERCUTANEOUS NEUROSTIMULATOR FOR MODULATING CARDIOVASCULAR FUNCTION," filed Oct. 11, 2006, which is hereby incorporated by reference its entirety.

TECHNICAL FIELD

This document relates generally to neurostimulation and particularly to a neurostimulation system for modulating cardiovascular function using an external neurostimulator and surface and/or percutaneous electrodes.

BACKGROUND

Neurostimulation has been applied or proposed to modulate various physiologic functions and treat various diseases. One example is the modulation of cardiovascular functions by stimulating sympathetic and parasympathetic nerves that innervate the heart. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the diastolic phase of a cardiac cycle. This ability of the vagal nerve stimulation may be utilized, for example, to control myocardial remodeling. Electrical stimulation applied at acupuncture points is also known to have therapeutic effects in cardiovascular functions.

Neurostimulation is known to provide therapeutic benefit when applied shortly after the occurrence of a cardiac disorder event such as acute MI. For example, after the acute MI, adverse ventricular remodeling starts and the heart is more susceptible to arrhythmias. Neurostimulation may be applied to control the post-MI ventricular remodeling and prevent the arrhythmias from occurring. Thus, there is a need for a neurostimulation system that can be deployed promptly following a cardiac disorder event such as acute MI. Because the post-MI neurostimulation may not be needed on a long-term and/or continuous basis, there is also a need for the neurostimulation system to be suitable for temporary and/or intermittent use.

SUMMARY

A neurostimulation device includes an external neurostimulator worn by a patient using a bracing element that braces a portion of the patient's body. The external neurostimulator delivers neurostimulation to modulate a cardiovascular function of the patient.

In one embodiment, a system for transcutaneous neurostimulation to modulate a cardiovascular function in a body includes a transcutaneous neurostimulation device configured to be worn on the body. The transcutaneous neurostimulation device includes surface stimulation electrodes configured to be placed on surface of the body, an external neurostimulator, and a bracing element. The external neurostimulator delivers neurostimulation transcutaneously to a stimulation target in the body through the surface stimulation electrodes. The bracing element braces a portion of the body to hold the external neurostimulator on a surface location of the body.

In one embodiment, a method is provided for modulating a cardiovascular function in a body by transcutaneous neurostimulation. An external neurostimulator is held on the body using a bracing element configured to brace a portion of the body. Surface stimulation electrodes are placed on the body, with at least one of the surface stimulation electrodes placed approximately over a stimulation target in the body. Neurostimulation is transcutaneously delivered to the stimulation target from the external neurostimulator through the surface stimulation electrodes. The delivery of the neurostimulation is controlled by executing a stimulation algorithm adapted to modulate the cardiovascular function.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 4 is an illustration of an embodiment of an external neurostimulator of the neurostimulation system.

FIG. 5 is an illustration of an embodiment of surface stimulation electrodes coupled to the external neurostimulator.

FIG. 6 is an illustration of another embodiment of surface stimulation electrodes coupled to the external neurostimulator.

FIG. 7 is an illustration of an embodiment of percutaneous stimulation electrodes coupled to the external neurostimulator.

FIG. 8 is an illustration of another embodiment of percutaneous stimulation electrodes coupled to the external neurostimulator.

FIG. 9 is an illustration of another embodiment of percutaneous stimulation electrodes coupled to the external neurostimulator.

FIG. 18 is an illustration of another embodiment of surface stimulation electrodes coupled to the external neurostimulator.

FIG. 19 is an illustration of an embodiment of surface and percutaneous stimulation electrodes coupled to the external neurostimulator.

FIG. 20 is an illustration of another embodiment of surface and percutaneous stimulation electrodes coupled to the external neurostimulator.

FIG. 21 is an illustration of another embodiment of surface and percutaneous stimulation electrodes coupled to the external neurostimulator.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a neurostimulation system including an external neurostimulator that modulate cardiovascular functions by delivering neurostimulation through transcutaneous and/or percutaneous electrodes. Implantable neurostimulation systems provide post-MI neurostimulation that has anti-remodeling and anti-arrhythmic effects. Recent data suggest maximum benefit to a patient suffering an acute MI is achieved when the neurostimulation is delivered within a week following the acute MI. The implantation of a neurostimulation system may require a substantially invasive operation that can be performed only by specially trained medical personnel. A long-term and/or continuous delivery of the neurostimulation may not be necessary or beneficial. For these and other reasons, a treatment using an implantable neurostimulation system may neither be made available when most needed nor be cost effective. To provide neurostimulation when an implantable neurostimulation system is unavailable, cost ineffective, or otherwise unsuitable, the present neurostimulation system uses an external neurostimulator coupled to transcutaneous and/or percutaneous electrodes. Such a system provides for a potentially fast therapy response to a cardiovascular disorder event such as acute MI and a potentially cost-effective means for delivering neurostimulation on a temporarily and/or intermittent basis.

Figure 1:
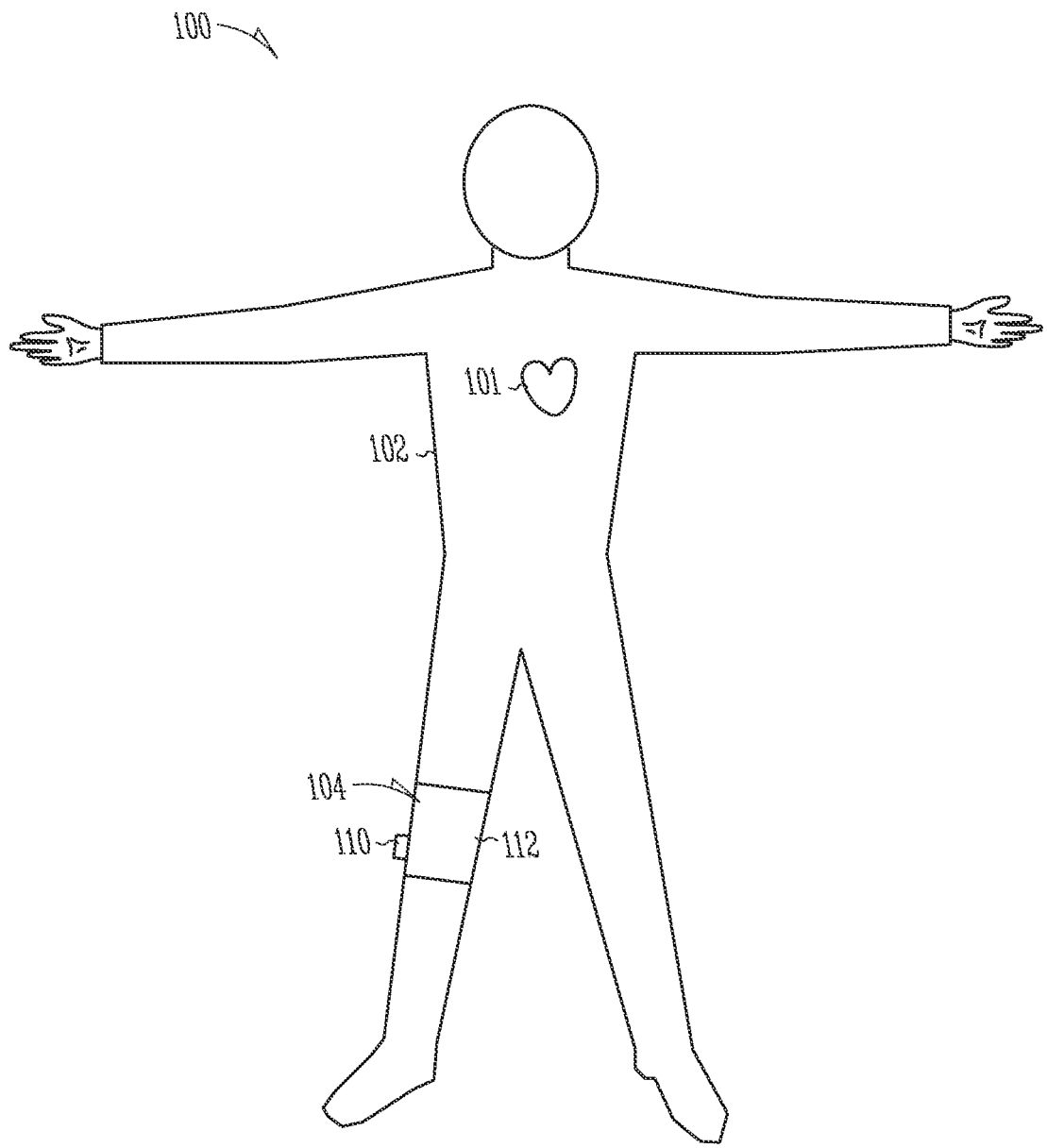
FIG. 1 is an illustration of an embodiment of a neurostimulation system and portions of an environment in which the neurostimulation system is used.

FIG. 1 is an illustration of an embodiment of a neurostimulation system 100 and portions of an environment in which system 100 is used. System 100 includes a neurostimulation device 104 configured to be worn on a body 102 of a patient. Neurostimulation device 104 includes an external neurostimulator 110 that delivers neurostimulation for modulating the patient's cardiovascular functions, a bracing element 112 to hold external neurostimulator 110 onto body 102 at a specified surface location, and electrodes through which the neurostimulation is delivered from external neurostimulator 110 to body 102. In one embodiment, neurostimulation device 104 is used as part of an emergency response to a cardiac disorder event occurring in the patient's heart 101, such as an acute MI. In another embodiment, neurostimulation device 104 is used for temporary or intermittent delivery of neurostimulation, such as when the implantation of a neurostimulation system is not justified.

In the illustrated embodiment, neurostimulation device 104 is donned over the knee area for stimulating the peroneal nerve at an acupuncture point known as GB-34 on the Gall Bladder Meridian of the foot. The acupuncture point GB-34 is also referred to as Yang Ling Quan (Yang Mound Spring) and about one inch below the knee, in the depression on the outer face of the shin, and corresponding to the point where the common peroneal nerve bifurcates into the superficial and deep peroneal nerves. Electrical stimulation at the acupuncture point GB-34 is known to have cardiovascular therapeutic effects such as being anti-remodeling, anti-hypertensive, and anti-arrhythmia. Potential results of electrical stimulation applied to the GB-34 include reduced heart rate, reduced blood pressure, and reduced arrhythmia vulnerability. In various embodiments, neurostimulation device 104 is used to treat a patient with cardiovascular diseases such as ischemic heart disease, heart failure, and hypertension.

Other acupuncture points known to have cardiovascular effects in response to electrical stimulation include PC-2 to PC-9 (on the Pericardium Meridian, running along the arm from below the armpit fold, along the transverse crease of the wrist, to the tip of the middle finger), HT-7 (on the Heart Meridian, on the transverse crease on the palm side of the wrist), BL-14 (on the Bladder Meridian, about 1.5 inches lateral to the lower border of the spinous process of the fourth thoracic vertebra), BL-16 (on the Bladder Meridian, about 1.5 inches lateral to the lower border of the spinous process of the sixth thoracic vertebra), and GV-11 (on the Governing Vessel Meridian, below the spinous process of the fifth thoracic vertebra).

In one embodiment, the neurostimulation device 104 is used to stimulate one or more nerves of the autonomic nervous system, such as to module heart rate and blood pressure. Stimulation of the vagus nerve following an acute MI is known to significantly reduce ventricular dilation following coronary artery ligation, manifested as decreased systolic and diastolic volumes.

In various embodiments, bracing element 112 includes a sleeve, a strap, or a belt configured to brace a portion of body 102, such as the knee, wrist, arm, leg, thigh, torso, neck, and head. Brace element 112 is adjustable in size and/or available in a plurality of sizes to accommodate patients with substantially different sizes.

In one embodiment, neurostimulation device 104 is a transcutaneous neurostimulation device. External neurostimulator 110 delivers the neurostimulation to a stimulation target in body 102 using surface stimulation electrodes placed on stimulation sites on the surface of body 102 approximately over the stimulation target. In one embodiment, such a transcutaneous neurostimulation device is made for donning by the patient or another person by following simple instructions. Examples of the surface stimulation electrodes used to deliver transcutaneous neurostimulation are discussed below with reference to FIGS. 5-6.

In another embodiment, neurostimulation device 104 is a percutaneous neurostimulation device. External neurostimulator 110 delivers the neurostimulation to a stimulation target in body 102 using at least one percutaneous stimulation electrode that is inserted into body 102 to lodge on or about a stimulation target in body 102. In one embodiment, such a percutaneous neurostimulation device is made available for use by emergency response medical personnel to provide neurostimulation immediately following an acute MI. In another embodiment, the percutaneous neurostimulation device is provided for temporary use while the patient is evaluated or waiting for a more permanent therapy such as an implantable device therapy. In another embodiment, the percutaneous neurostimulation device is used when the stimulation target is difficult to reach by the transcutaneous neurostimulation, thereby expanding the range of potential stimulation targets. Examples of the percutaneous stimulation electrodes used to deliver percutaneous neurostimulation are discussed below with reference to FIGS. 7-11.

Figure 2:
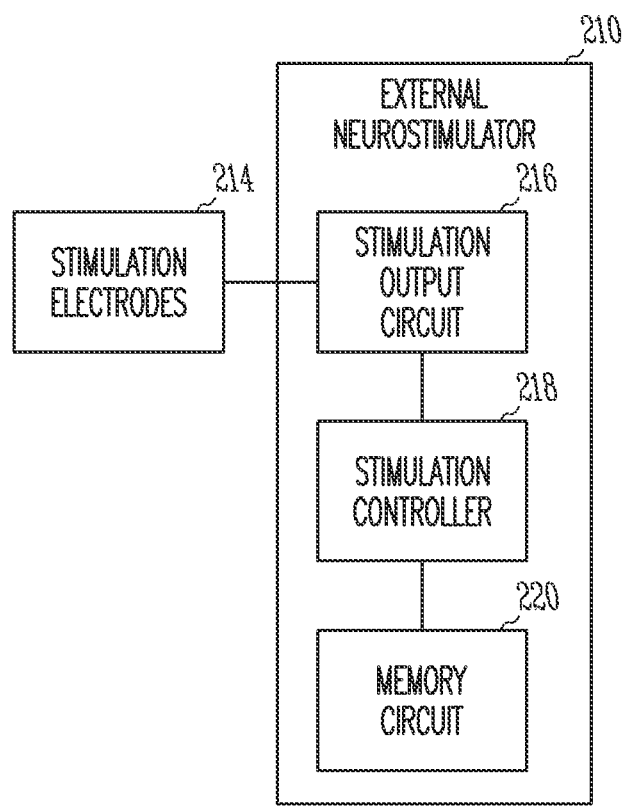
FIG. 2 is a block diagram illustrating an embodiment of portions of a circuit of the neurostimulation system.

FIG. 2 is a block diagram illustrating an embodiment of portions of a circuit of system 100, including stimulation electrodes 214 and an external stimulator 210. In one embodiment, stimulation electrodes 214 include surface stimulation electrodes. In another embodiment, stimulation electrodes 214 include percutaneous stimulation electrodes. In another embodiment, stimulation electrodes 214 include transcutaneous and percutaneous stimulation electrodes.

External neurostimulator 210 is a specific embodiment of external neurostimulator 110 and includes a stimulation output circuit 216, a stimulation controller 218, and a memory circuit 220. Stimulation output circuit 216 is electrically coupled to stimulation electrodes 214 and delivers the neurostimulation to a stimulation target in body 102 through stimulation electrodes 214. Stimulation controller 218 controls the delivery of the neurostimulation by executing a stimulation algorithm for modulating a cardiovascular function. Memory circuit 220 stores the stimulation algorithm including stimulation parameters.

Figure 3:
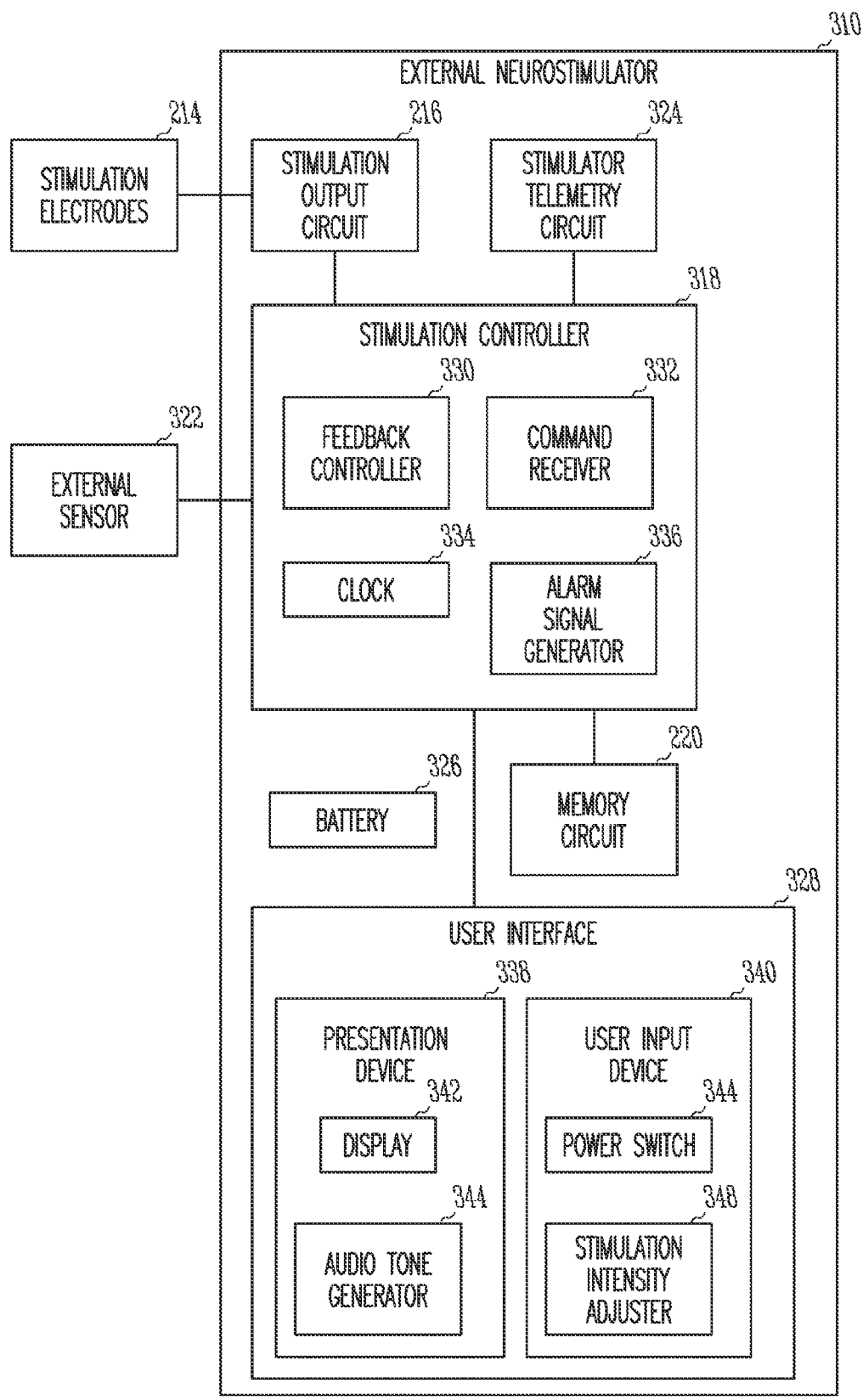
FIG. 3 is a block diagram illustrating another embodiment of portions of the circuit the neurostimulation system.

FIG. 3 is a block diagram illustrating another embodiment of portions of the circuit of system 100, including stimulation electrodes 214, an external neurostimulator 310, and an external sensor 322. External neurostimulator 310 is a specific embodiment of external neurostimulator 210 and includes stimulation output circuit 216, a stimulation controller 318, a stimulator telemetry circuit 324, a battery 326, and a user interface 328.

Stimulation output circuit 216 delivers neurostimulation through stimulation electrodes 214. In one embodiment, the neurostimulation is in the form of electrical pulses. In other embodiments, the neurostimulation includes any form of energy that is capable of eliciting action potentials in a target nerve, such as magnet field, light, and ultrasound.

Stimulation controller 318 is a specific embodiment of stimulation controller 218 and controls the delivery of the neurostimulation by executing a stimulation algorithm for modulating a cardiovascular function. The stimulation algorithm includes stimulation parameters selected to modulate the cardiovascular function. Examples of the stimulation parameters for controlling the delivery of electrical neurostimulation pulses include pulse amplitude, pulse width, stimulation frequency (or inter-pulse interval), periodic dose, and duty cycle. The pulse amplitude and pulse width are selected to ensure that each pulse elicits an action potential in the target nerve. In one embodiment, the stimulation frequency is between approximately 0.1 and 200 Hz, with between approximately 1 and 30 Hz as a specific example for modulating cardiovascular functions. In one embodiment, in which the electrical neurostimulation pulses are delivered transcutaneously using surface electrodes, the stimulation frequency is between approximately 1 and 5 Hz. In one embodiment, in which the electrical neurostimulation pulses are delivered percutaneously using at least one percutaneous electrode, the stimulation frequency is between approximately 1 and 50 Hz. The periodic dose is a time interval during which a patient is treated with neurostimulation for each predetermined period. In one embodiment, the predetermined period is a day, and the periodic dose is a daily dose. The duty cycle is the duty cycle of the neurostimulation during the time interval during of the period dose. For example, if the patient is to receive a neurostimulation therapy for two hours each day, the periodic dose is 2 hours/day (or the daily dose is 2 hours). If the neurostimulation during those two hours is delivered intermittently with alternating on- and off-periods, the duty cycle is the ratio of the on-period to the sum of the on-period and the off-period. In one embodiment, the daily dose is between approximately 0.5 and 24 hours. In one embodiment, the duty cycle is between approximately 10 and 50%. The on-period is between approximately 10 and 120 seconds, and the off-period is between approximately 50 and 120 seconds.

In the illustrated embodiment, stimulation controller 318 includes a feedback controller 330, a command receiver 332, a clock 334, and an alarm signal generator 336. In various embodiments, stimulation controller 318 includes one or more of feedback controller 330, command receiver 332, clock 334, and alarm signal generator 336. Feedback controller 330 controls the delivery of the neurostimulation using a feedback control signal that indicates a need to start, stop, or adjust the neurostimulation. In one embodiment, the feedback control signal provides for automatic verification of neural response to the neurostimulation. In one embodiment, external sensor 322 senses the feedback control signal. In a specific embodiment, external sensor 332 is a sensor included in external neurostimulator 310. In another specific embodiment, external sensor 332 is electrically connected to external neurostimulator 310. In another specific embodiment, external sensor 332 is communicatively coupled to external neurostimulator 310 via telemetry. Examples of external sensor 322 include a heart rate sensor to sense a heart rate, a pressure sensor to measure a blood pressure, and a plethysmographic sensor to sense plethysmogram signal. In another embodiment, feedback controller 330 receives the feedback control signal from stimulator telemetry circuit 324. Another device, such as an implantable device in body 102 or an external device, senses the feedback control signal and telemeters the feedback control signal to external neurostimulator 310.

Command receiver 332 receives a stimulation command for starting, pausing, or stopping the delivery of the neurostimulation. In one embodiment, the stimulation command is received from another device. In another embodiment, the stimulation command is received from user interface 328. Clock 334 keeps track of the time. In one embodiment, clock 334 times the delivery of a neurostimulation therapy according to a programmed schedule. For example, when the patient is to receive a periodic dose according to the programmed schedule, clock 334 produces a stimulation command and transmits the stimulation command to command receiver 332 to starting the delivery of the neurostimulation. Alarm signal generator 336 generates an alarm signal to remind the patient or another person that the patient is due for receiving the periodic dose of the neurostimulation. In one embodiment, alarm signal generator 336 generates an alarm signal indicating a problem or potential problem with external neurostimulator 310, such as a low battery level. In another embodiment, alarm signal generator 336 an audio tone as an auditory feedback signal confirming that the neurostimulation delivered from external neurostimulator 310 is producing desirable result, such as indicated by the feedback control signal.

Memory circuit 220 stores the stimulation algorithm including the stimulation parameters. In one embodiment, memory circuit 220 also stores the history of delivery of the neurostimulation. In one example, the patient is given a transcutaneous neurostimulation device and instructed to apply the neurostimulation according to a treatment schedule. If the patient is due to receive the treatment, but the transcutaneous neurostimulation device is not worn or turned on, alarm signal generator 336 generates an alarm signal as a reminder to the patient.

User interface 328 includes a presentation device 338 and a user input device 340. Presentation device 338 includes a display 342 and an audio tone generator 344. In one embodiment, display 342 a liquid crystal display (LCD) screen. Display 342 displays information including, but not limited to, power on/off status of the external neurostimulator, parameters produced using signal sensed by external sensor 322 (such as the heart rate and the blood pressure), the time, and the battery status. User input device 340 includes a power switch 346 and a stimulation intensity adjuster 348. Power switch 328 allows the patient or another person to turn external neurostimulator 310 on and off. Stimulation intensity adjuster 348 allows the patient or another person to adjust the stimulation parameters to change the intensity of the neurostimulation. In one embodiment, display 342 indicates whether the neurostimulation elicits an expected response, and the patient can use stimulation intensity adjuster 348 to change the intensity of the neurostimulation if the current intensity causes discomfort. In another embodiment, feedback controller 330 adjusts the intensity of the neurostimulation automatically using the feedback control signal such that stimulation intensity adjuster 348 is unnecessary.

Battery 326 supplies the power for the operation of the circuit of external neurostimulator 310. In one embodiment, battery 326 is a rechargeable battery. In one embodiment, the patient using system 100 is provided with a battery charger that uses standard AC power. When needed, the battery charger is equipped with one or more adaptors for use in different countries.

FIG. 4 is an illustration of an embodiment of an external neurostimulator 410, which is a specific embodiment of external neurostimulator 110. FIG. 4 shows a front view of external neurostimulator 410, which includes a chassis 454 to house a circuit such as the circuit of external neurostimulator 210 or 310. A user interface including a display 442 and user input device 440 are incorporated onto chassis 454. Display 442 represents an embodiment of display 342. User input device 440 represents an embodiment of user input device 340 and includes buttons, knobs, and/or other switches that are operated by the patient or another person.

FIG. 5 is an illustration of an embodiment of surface stimulation electrodes coupled to external neurostimulator 410. FIG. 5 shows a rear view of external neurostimulator 410. Surface stimulation electrodes 556A-B are incorporated onto the side of chassis 454 that is in contact of the surface of body 102 when being used. External neurostimulator 410 is placed on a surface location of body 102 such that surface stimulation electrodes 556A-B are positioned approximately over a stimulation target in body 102. In one embodiment, surface stimulation electrodes 556A-B each have a surface area between approximately 5 and 100 mm$^2$.

In the illustrated embodiment, surface stimulation electrodes 556A-B are shown as disc electrodes for illustrate purposes only. Other examples of the configuration of surface stimulation electrodes 556A-B include strip electrodes, ring electrodes, and concentric electrodes.

FIG. 6 is an illustration of another embodiment of surface stimulation electrodes coupled to external neurostimulator 410. Surface stimulation electrodes 656A-B are each connected to external neurostimulator 410 using a lead. In the illustrated embodiment, surface stimulation electrodes 656A is connected to external neurostimulator 410 using a lead 658A, and is incorporated onto a skin patch 659A. Surface stimulation electrodes 656B is connected to external neurostimulator 410 using a lead 658B, and is incorporated onto a skin patch 659B. Skin patches 659A-B are attached to the surface of body 102 using adhesive. In another embodiment, surface stimulation electrodes 656A-B are incorporated onto a single skin patch and connected to external neurostimulator 410 using a multi-conductor lead.

FIG. 7 is an illustration of an embodiment of percutaneous stimulation electrodes coupled to external neurostimulator 410. Percutaneous stimulation electrodes 756A-B are each configured to pierce the skin of body 102 and lodge in a specified stimulation site in body 102. The specific stimulation site is on or about a target nerve.

Percutaneous stimulation electrodes 756A-B are each a wire electrode including a wire having a proximal end coupled to external neurostimulator 410 and a distal end configured to lodge in the specified stimulation site in body 102. In one embodiment, the wire includes a coiled portion such that when each of electrodes 756A-B exits body 102, the wire is coiled as it exits the skin The coiled portion is employed to reduce the likelihood of infection with percutaneous wires because greater mechanical stability and encapsulation are achieved with the coiled wire. In the illustrated embodiment, the wire electrode is a needle electrode, where the wire is substantially rigid. The distal end is a sharp tip suitable for penetrating tissue and includes barbs (760A or 760B) to provide a stable electrode placement. In the illustrated embodiment, percutaneous stimulation electrodes 756A-B are mounted on and projecting from external neurostimulator 410. In another embodiment, percutaneous stimulation electrodes 756A-B are each connected to external neurostimulator 410 using a lead.

FIG. 8 is an illustration of an embodiment of percutaneous stimulation electrodes coupled to external neurostimulator 410. Percutaneous stimulation electrodes 856A-B are each a wire electrode including a wire having a proximal end coupled to external neurostimulator 410 and a distal end configured to lodge in the specified stimulation site in body 102. In one embodiment, the wire includes a coiled portion such that when each of electrodes 856A-B exits body 102, the wire is coiled as it exits the skin In the illustrated embodiment, the wire electrode is a flexible electrode, where the wire is substantially flexible. Percutaneous stimulation electrodes 856A-B each includes a distal end that is a J-shaped hook (860A or 860B). In one embodiment, percutaneous stimulation electrodes 856A-B are each introduced into tissue with a hollow needle.

FIG. 9 is an illustration of an embodiment of percutaneous stimulation electrodes coupled to external neurostimulator 410. An implantable capsule 962 includes percutaneous stimulation electrodes 956A-B each on one of its opposite ends. To deliver the neurostimulation, capsule 962 is subcutaneously implanted, and a multi-conductor lead 958 provides percutaneous connections between each of percutaneous stimulation electrodes 956A-B and external neurostimulator 410. In one embodiment, capsule 962 has a cylindrical elongate body coupled between opposite ends. The length of capsule between the opposite ends is between approximately 5 mm and 25 mm. The cylindrical elongate body has a diameter between approximately 1 mm and 10 mm. In one embodiment, capsule 962 is implanted by injection through a hollow injection device having an end configured to reach the stimulation target in body 102. Examples of the hollow injection device include a hollow needle and hollow catheter.

Figure 10:
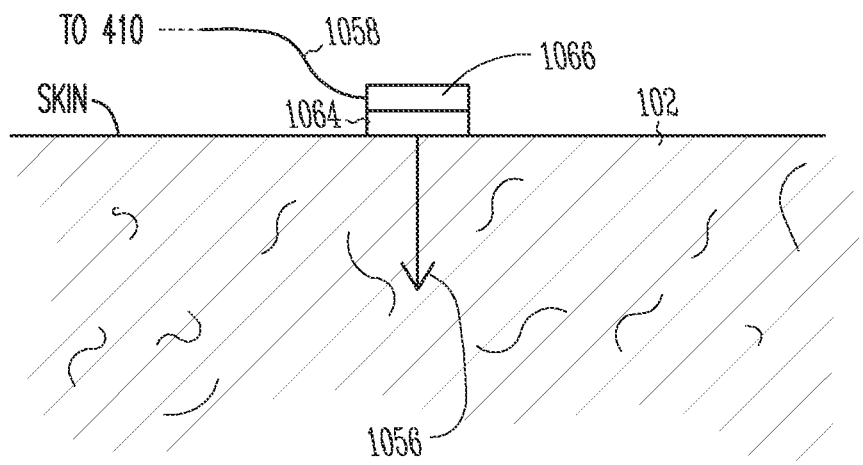
FIG. 10 is an illustration of an embodiment of a percutaneous stimulation electrode coupled to the external neurostimulator through a skin-mounted connector.

FIG. 10 is an illustration of an embodiment of a percutaneous stimulation electrode 1056 coupled to external neurostimulator 410 through a skin-mounted connector 1064. Connector 1064 includes a button mounted on a surface location of body 102 and is electrically connected to percutaneous stimulation electrode 1056. Connector 1066 is to be connected to connector 1064 and to external neurostimulator 410 through a lead 1058. In one embodiment, connectors 1064 and 1066 are button-connectors allowing for a snap-on connection. In another embodiment, connectors 1064 and 1066 are flat discs including magnets to hold to each other magnetically. In another embodiment, connectors 1064 and 1066 are a pair of slot and groove slide-in connectors with latch and push-button release. The use of connectors 1064 and 1066 allows external neurostimulator 410 to be disconnected from percutaneous stimulation electrode 1056, for example, when the patient is not treated with the neurostimulation. The use of these connectors also provide mechanical strain relief. In various embodiments, percutaneous stimulation electrode 1056 includes any electrode suitable for implantation in body 102 to deliver the neurostimulation, with electrode 756A/B being a specific example.

Figure 11:
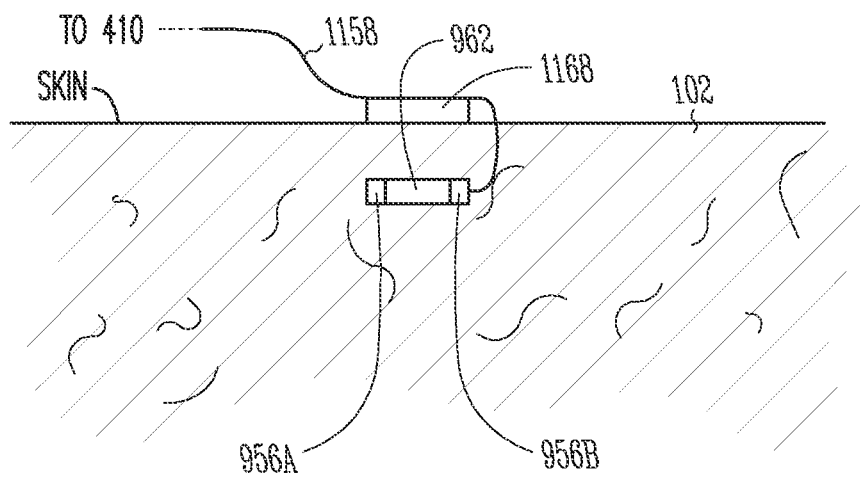
FIG. 11 is an illustration of an embodiment of a percutaneous stimulation electrode coupled to the external neurostimulator through a lead with a magnet.

FIG. 11 is an illustration of an embodiment of a percutaneous stimulation electrode coupled to external neurostimulator 410 through a lead 1158 with a magnet 1168. Capsule 962, which includes percutaneous stimulation electrodes 956A-B, is to be electrically connected to external neurostimulator 410 through lead 1158. Magnet 1168 is coupled to lead 1158 and is to be placed onto a surface location of body 102 over implanted capsule 962 to prevent capsule 962 from drifting in the tissue.

FIGS. 5-11 illustrate various stimulation electrode configurations as specific examples of surface and percutaneous stimulation electrodes. A transcutaneous neurostimulation device includes at least a pair of surface stimulation electrode. A percutaneous neurostimulation device includes at least one percutaneous stimulation electrode. In one embodiment, the neurostimulation is delivered using a pair of percutaneous stimulation electrodes. In another embodiment, the neurostimulation is delivered using a percutaneous stimulation electrode placed on or about the stimulation target and a surface stimulation electrode serving as a return electrode. Some additional examples of electrode configurations are discussed below with reference to FIGS. 18-21. In various embodiments, neurostimulation is delivered transcutaneously or percutaneously using a pair of stimulation electrodes selected from any of those illustrated in FIGS. 5-11 as well as any other suitable surface and percutaneous electrodes.

Figure 12:
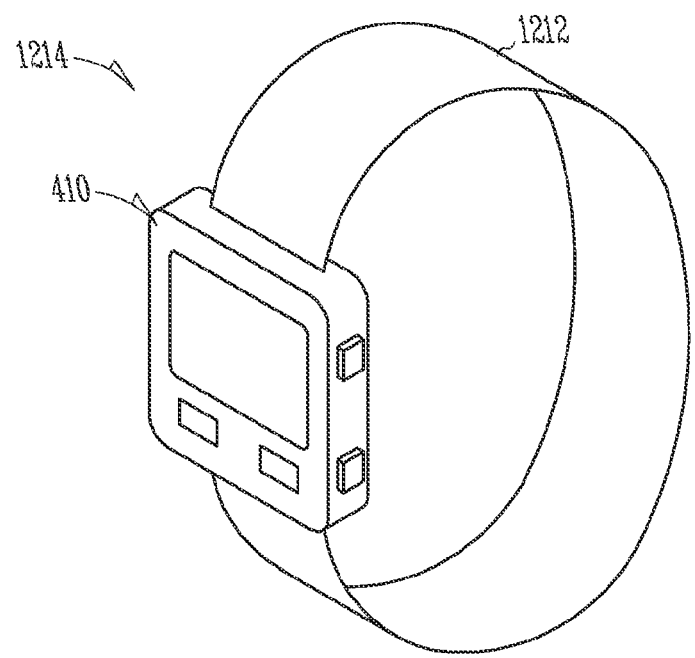
FIG. 12 is an illustration of an embodiment of the external neurostimulator coupled to a bracing element.

FIG. 12 is an illustration of an embodiment of external neurostimulator 410 coupled to a bracing element. A neurostimulation device 1214 includes external neurostimulator 410 affixed to a bracing element 1212. Bracing element 1212 is configured to brace a portion of body 102 to hold external neurostimulator 410 onto the surface of body 102. In one embodiment, in which neurostimulation device 1214 is a transcutaneous neurostimulation device, bracing element 1212 allows surface stimulation electrodes on external neurostimulator 410 (such as electrodes 556A-B) to be placed securely on a surface location of body 102 approximately over a stimulation target in body 102. In another embodiment, in which neurostimulation device 1214 is a percutaneous neurostimulation device, bracing element 1212 allows external neurostimulator 410 to be worn on a surface location of body 102 over or near a stimulation target in body 102 on or about which at least one percutaneous stimulation electrode is lodged. In the illustrated embodiment, bracing element 1212 includes a belt. In one embodiment, belt 1212 is detachably coupled to external neurostimulator 410. In one embodiment, belt 1212 has an adjustable length. In one embodiment, belt 1212 includes a wrist band, and neurostimulation device 1214 has a configuration similar to a wrist watch. In other embodiments, belt 1212 has a length suitable for bracing another portion of body 102, such as the knee, arm, leg, thigh, torso, neck, or head.

Figure 13:
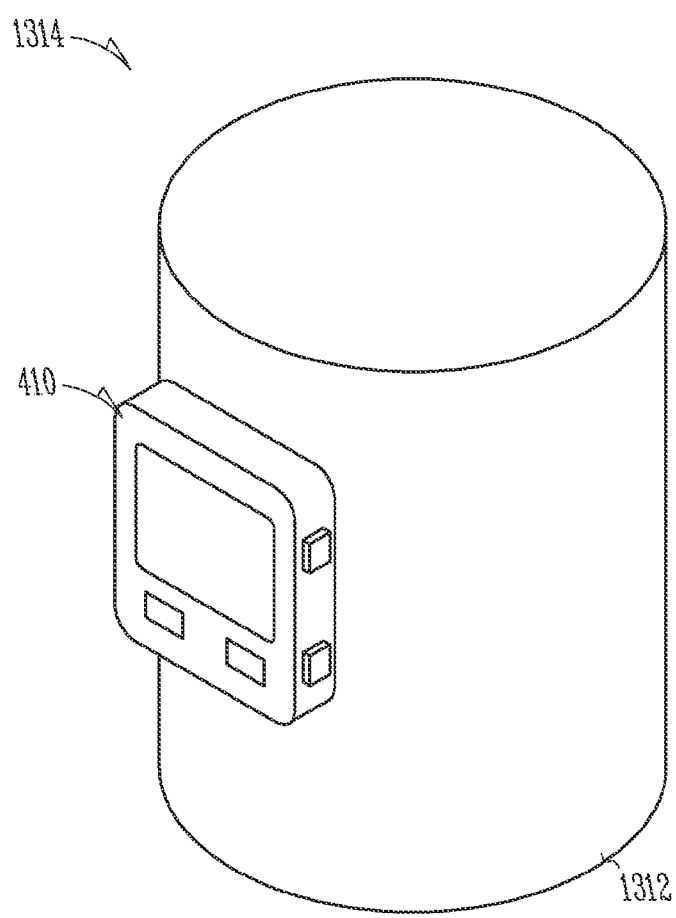
FIG. 13 is an illustration of another embodiment of the external neurostimulator coupled to a bracing element.

FIG. 13 is an illustration of another embodiment of external neurostimulator 410 coupled to a bracing element. An neurostimulation device 1314 includes external neurostimulator 410 affixed to a bracing element 1312, which has substantially same functions as bracing element 1212 except for being a sleeve. The choice between using belt 1212 and sleeve 1312 may depend on factors such as location on body 102 and patient preference. In one embodiment, sleeve 1312 is detachably coupled to external neurostimulator 410. In one embodiment, sleeve 1312 is made of an elastic material to provide an adjustable length. In one embodiment, sleeve 1312 includes a knee sleeve, and neurostimulation device 1314 is worn as a knee guard. In other embodiments, sleeve 1312 has a length suitable for bracing another portion of body 102, such as the wrist, arm, leg, thigh, torso, neck, or head.

External neurostimulator 410 is illustrated in FIGS. 4-9, 12, and 13 as a specific example and not as a restriction. In various embodiments, the external neurostimulator of the present neurostimulation system may have any configuration suitable for being incorporated into a neurostimulation device worn by the patient, such as neurostimulation device 104, to deliver transcutaneous and/or percutaneous neurostimulation as discussed in this document.

Figure 14:
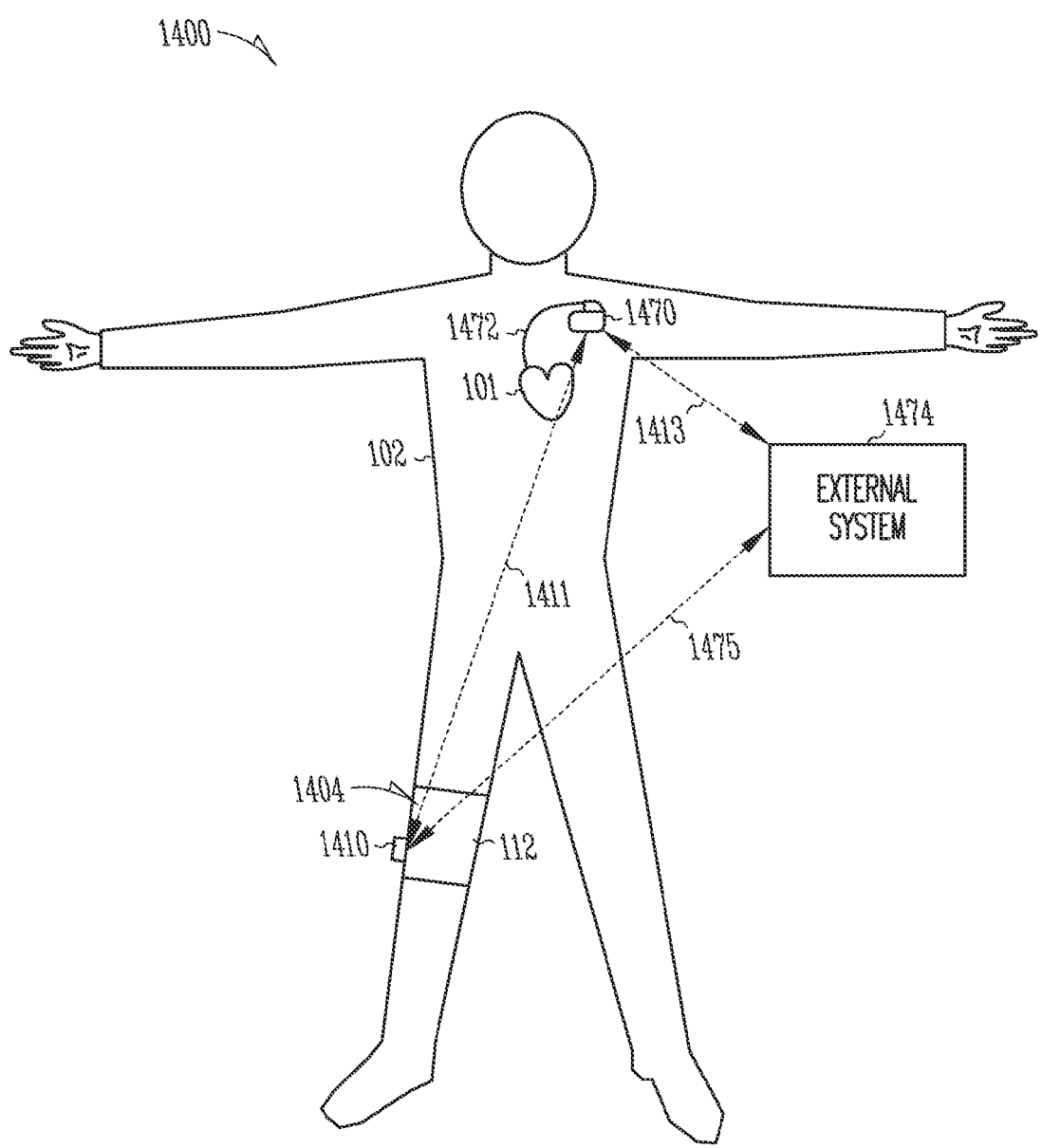
FIG. 14 is an illustration of an embodiment of a neurostimulation system including a neurostimulation device, an implantable medical device, and an external system.

FIG. 14 is an illustration of an embodiment of a neurostimulation system 1400. System 1400 includes a neurostimulation device 1404, an implantable medical device 1470, and an external system 1474. Neurostimulation device 1404 is a specific embodiment of neurostimulation device 104 and includes an external neurostimulator 1410 coupled to bracing element 112. In one embodiment, external neurostimulator 1410 includes the circuit of external neurostimulator 310 as discussed above. A telemetry link 1411 provides for communication between external neurostimulator 1410 and implantable medical device 1470. A telemetry link 1413 provides for communication between implantable medical device 1470 and external system 1474. A telemetry link 1475 provides for communication between external neurostimulator 1410 and external system 1474.

In one embodiment, implantable medical device 1470 includes an implantable cardiac rhythm management (CRM) device. Implantable medical device 1470 includes, but is not limited to, one or more of a pacemaker, a cardioverter/defibrillator, a cardiac resynchronization therapy device, a cardiac remodeling control therapy device, a neurostimulation device, a drug delivery device, a biologic therapy device, and a patient monitoring device. A lead system 1472 includes one or more leads providing for electrical and/or other connections between heart 101 and implantable medical device 110.

External system 1474 allows for programming of implantable medical device 1470 and/or external neurostimulator 1410 and receives signals acquired by implantable medical device 1470 and/or external neurostimulator 1410. In one embodiment, external system 1474 includes a programmer. In another embodiment, external system 1474 is a patient management system including an external device in proximity of body 102 (in which implantable medical device 1470 is implanted and on which neurostimulation device 1404 is worn), a remote device in a relatively distant location, and a telecommunication network linking the external device and the remote device. The patient management system allows for access to implantable medical device 1470 and/or external neurostimulator 1410 from a remote location, such as for monitoring patient status, adjusting therapies, and obtaining patient's medical records stored in a remote location.

Telemetry link 1413 is a wireless communication link providing for data transmission between implantable medical device 1470 and external system 1474. Telemetry link 1413 provides for data transmission from implantable medical device 1470 to external system 1474. This may include, for example, transmitting real-time physiological data acquired by implantable medical device 1470, extracting physiological data acquired by and stored in implantable medical device 1470, extracting therapy history data stored in implantable medical device 1470, and extracting data indicating an operational status of implantable medical device 1470 (e.g., battery status and lead impedance). Telemetry link 1413 also provides for data transmission from external system 1474 to implantable medical device 1470. This may include, for example, programming implantable medical device 1470 to acquire physiological data, programming implantable medical device 1470 to perform at least one self-diagnostic test (such as for a device operational status), programming implantable medical device 1470 to enable an available monitoring or therapeutic function, and programming implantable medical device 1470 to adjust therapeutic parameters such as pacing and/or cardioversion/defibrillation parameters.

Telemetry link 1475 is a wireless communication link providing for data transmission between external neurostimulator 1410 and external system 1474. Telemetry link 1475 provides for data transmission from external neurostimulator 1410 to external system 1474. This may include, for example, transmitting real-time physiological data acquired by external neurostimulator 1410, extracting physiological data acquired by and stored in external neurostimulator 1410, extracting therapy history data stored in external neurostimulator 1410, and extracting data indicating an operational status of external neurostimulator 1410 (e.g., battery status). Telemetry link 1475 also provides for data transmission from external system 1474 to external neurostimulator 1410. This may include, for example, programming external neurostimulator 1410 to adjust the stimulation parameters, and transmitting a user command to external neurostimulator 1410 to initiate a delivery of the neurostimulation.

Telemetry link 1411 is a wireless communication link providing for data transmission between external neurostimulator 1410 and implantable medical device 1470. Telemetry link 1475 provides for data transmission from implantable medical device 1470 to external neurostimulator 1410. This may include, for example, transmitting a signal sensed by implantable medical device 1470 to external neurostimulator 1410 for use as the feedback control signal controlling the neurostimulation, and transmitting a neurostimulation command to external neurostimulator 1410 to initiate a delivery of the neurostimulation, such as when a predetermined-type cardiac event is detected by implantable medical device 1470. In one embodiment, telemetry link 1475 also provides for data transmission from external neurostimulator 1410 to implantable medical device 1470.

System 1400 allows the neurostimulation to be initiated by any one of external neurostimulator 1410, implantable medical device 1470, and external system 1474. In one embodiment, external neurostimulator 1410 and/or implantable medical device 1470 initiate a neurostimulation therapy upon detecting a predetermined signal or condition. External system 1474 initiates a neurostimulation therapy upon receiving a user command.

Figure 15:
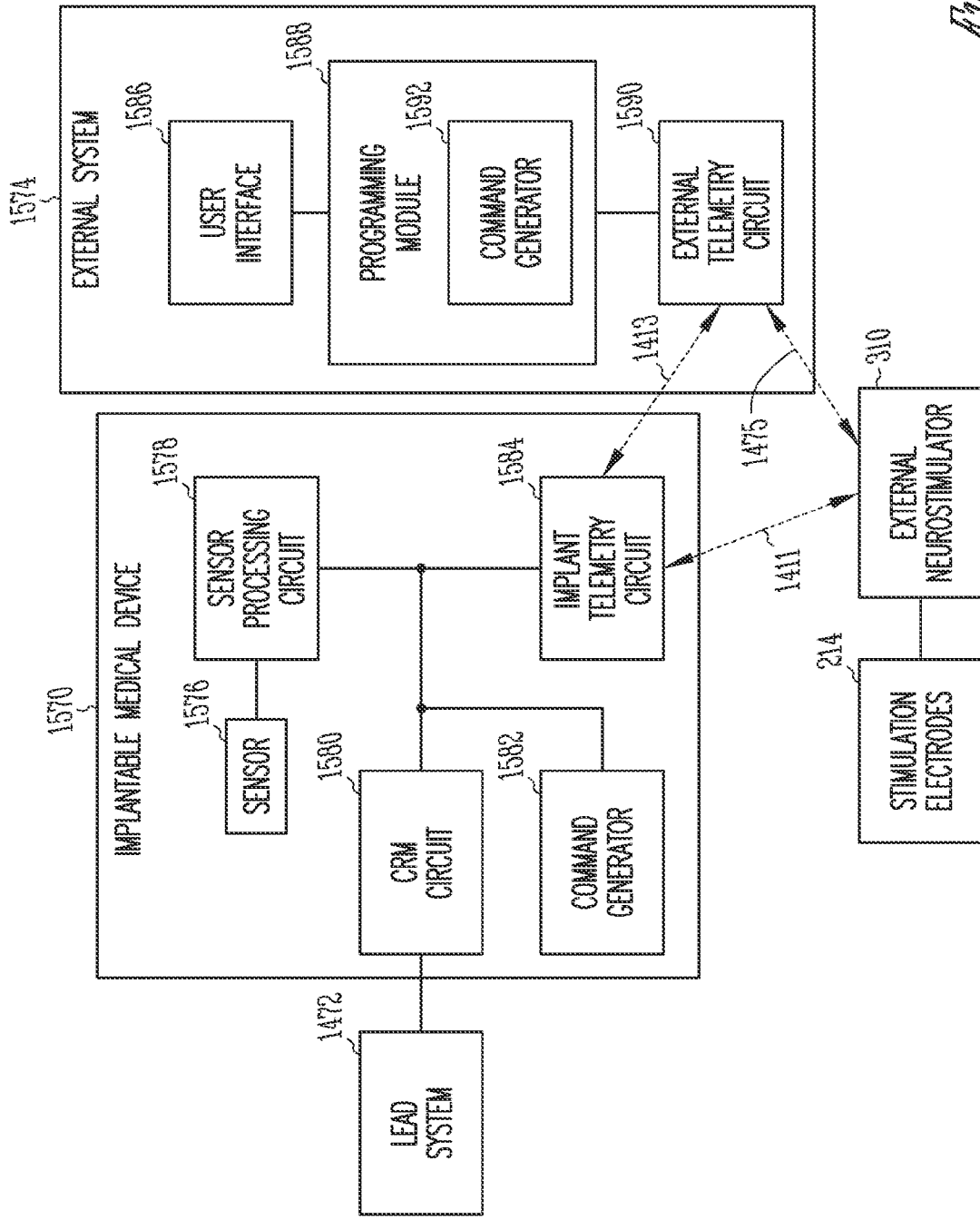
FIG. 15 is a block diagram illustrating an embodiment of portions of a circuit of the neurostimulation system of FIG. 14.

FIG. 15 is a block diagram illustrating an embodiment of portions of a circuit of system 1400. The circuit includes an implantable medical device 1570 coupled to lead system 1472, an external system 1574, and external neurostimulator 310 coupled to stimulation electrodes 214.

Implantable medical device 1570 is a specific embodiment of implantable medical device 1470 and includes a CRM circuit 1580, a sensor 1576, a sensor processing circuit 1578, a command generator 1582, and an implant telemetry circuit 1584. CRM circuit 1580 delivers one or more CRM therapies. In one embodiment, CRM circuit 1580 includes one or more of a pacemaker and a cardioverter/defibrillator to delivery cardiac electrical stimulation to heart 101 through lead system 1472. Sensor 1576 senses a physiologic signal. Sensor processing circuit 1578 produces the feedback control signal used by feedback controller 330 of external neurostimulator 310 using the sensed physiologic signal. In one embodiment, the physiological signal is a cardiac signal, and the feedback control signal is indicative of a cardiac condition to be modulated by the neurostimulation. Command generator 1582 produces the neurostimulation command that initiates a neurostimulation therapy, such as upon detecting a specified-type cardiac event (such as ischemia or MI) from the cardiac signal. Implant telemetry circuit 1584 transmits the feedback control signal and/or the neurostimulation command to the external neurostimulator 310.

External system 1574 includes a user interface 1586, a programming module 1588, and an external telemetry circuit 1590. User interface 1586 allows a user such as a physician or other caregiver to program implantable medical device 1570 and/or external neurostimulator 310 and observe signals acquired by implantable medical device 1470 and/or external neurostimulator 310. Programming module 1588 converts user input received by user interface 1586 to programming codes to be transmitted to implantable medical device 1470 and/or external neurostimulator 310 by external telemetry circuit 1590. In the illustrated embodiment, user interface 1586 allows the user to enter the user command for initiating a neurostimulation therapy, and programming module 1588 includes a command generator 1592 to produce the neurostimulation command upon receiving the user command for initiating the neurostimulation therapy. External telemetry circuit 1590 transmits the neurostimulation command to external neurostimulator 310.

Figure 16:
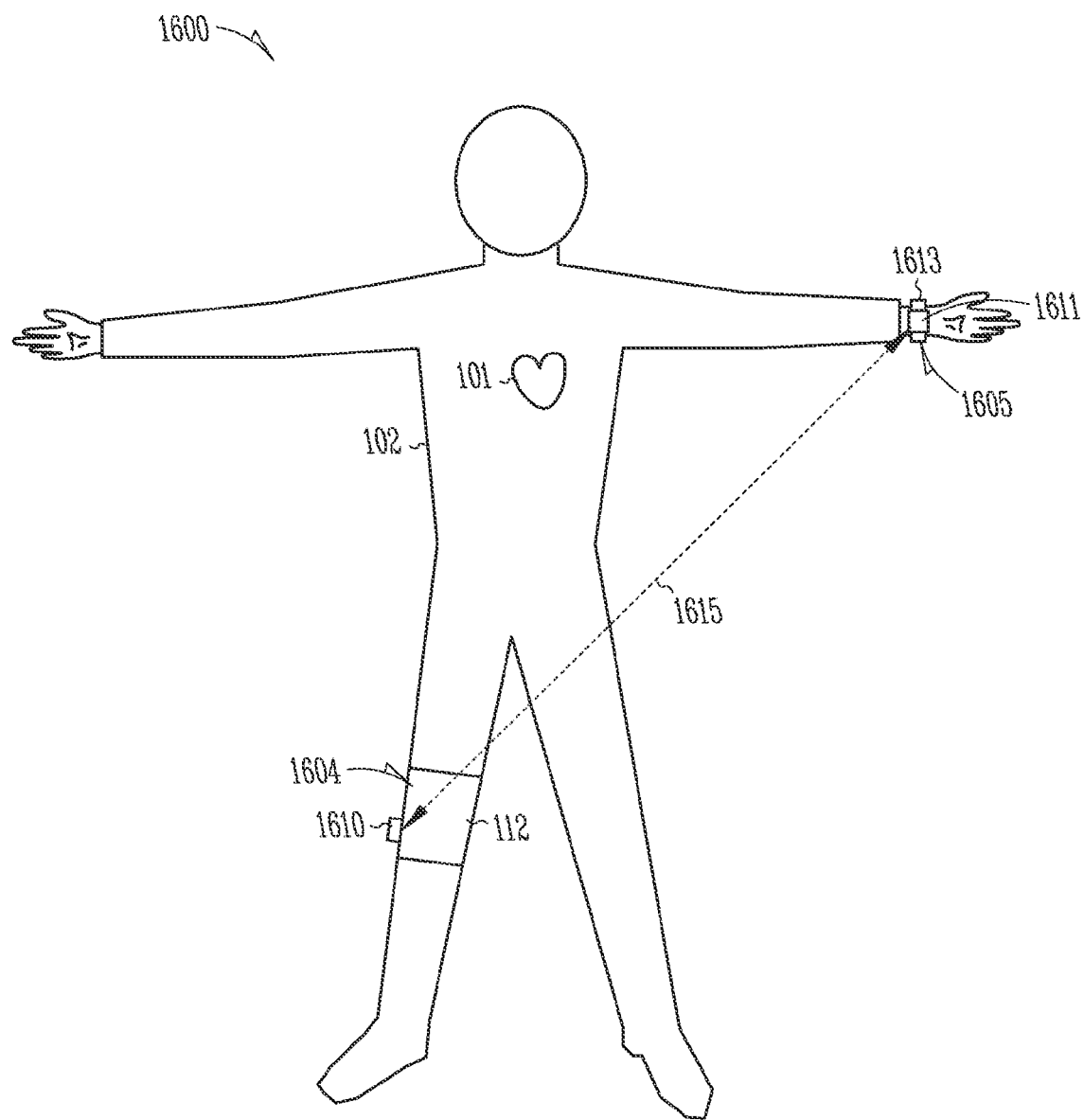
FIG. 16 is an illustration of an embodiment of a neurostimulation system including a neurostimulation device and a user communication device.

FIG. 16 is an illustration of an embodiment of a neurostimulation system 1600. System 1600 includes a neurostimulation device 1604 and a user communication device 1605. Neurostimulation device 1604 is a specific embodiment of neurostimulation device 104 and includes an external neurostimulator 1610 coupled to bracing element 112. User communication device 1605 includes a communicator 1611 and a bracing element 1613. In one embodiment, external neurostimulator 1610 includes substantially the circuit of external neurostimulator 310 except user interface 328, which is included in communicator 1611. A telemetry link 1615 provides for communication between external neurostimulator 1610 and communicator 1611. System 1600 provides for easy access to and observation of a user interface when the external stimulator is held onto a bodily location that is not convenient to reach and see by at least the patient wearing the external stimulator, such as the knee or the neck. User communication device 1605 is a portable device that is carried or worn by the patient in a way allowing for convenient access by the patent. When user communication device 1605 is worn by the patient, bracing element 1613 holds communicator 1611 on body 102 by bracing a portion of body 102, such as the lower arm or wrist. In the illustrated embodiment, neurostimulation device 1604 is configured to be worn on the knee area, such as for stimulating the peroneal nerve at the acupuncture point GB-34, and user communication device 1605 is configured to be worn on a wrist, in the form of a wrist watch. In a specific embodiment, user communication device 1605 has the appearance of the neurostimulation device 1214 as illustrated in FIG. 12.

Figure 17:
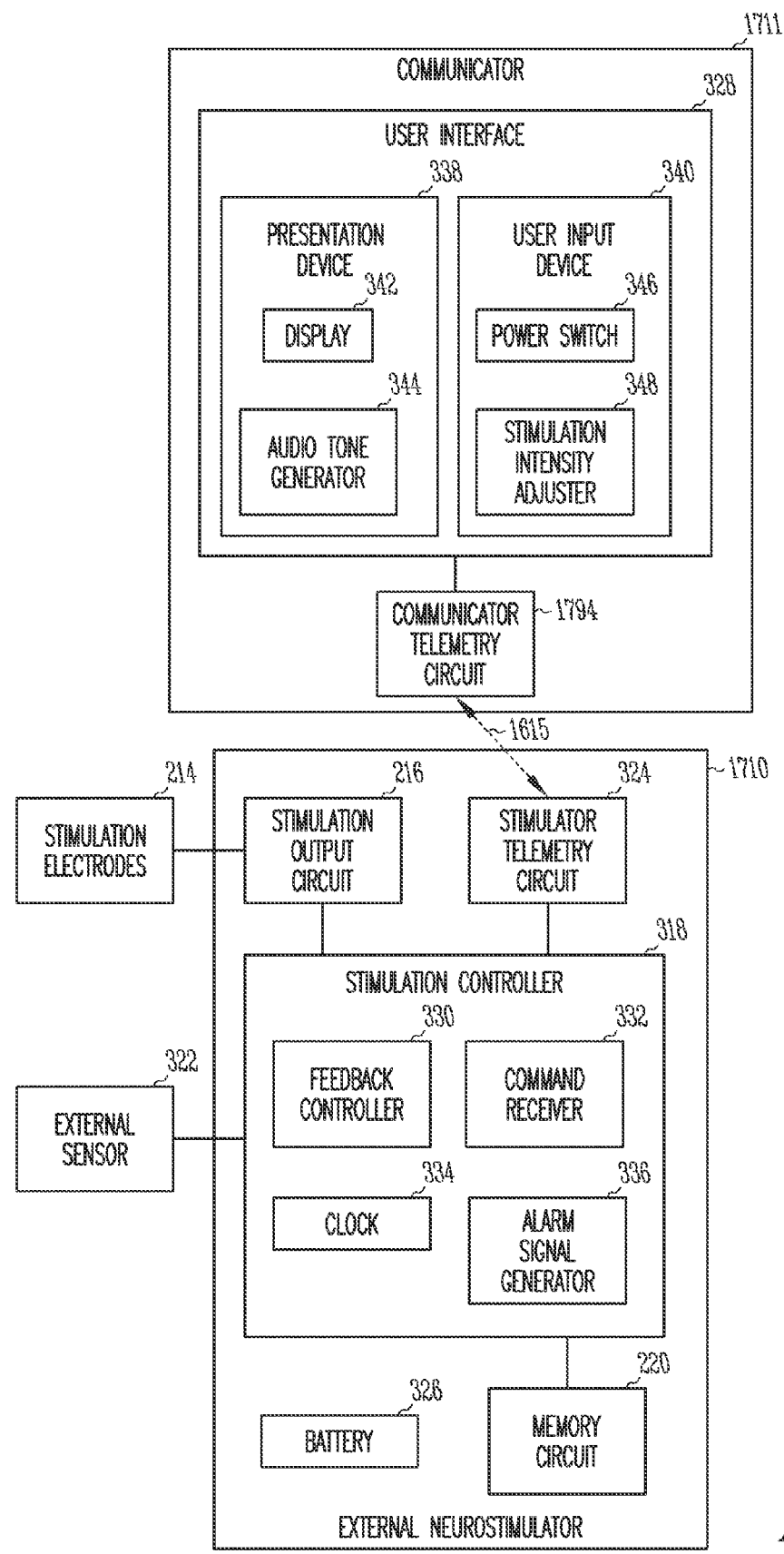
FIG. 17 is a block diagram illustrating an embodiment of portions of a circuit of the neurostimulation system of FIG. 16.

FIG. 17 is a block diagram illustrating an embodiment of portions of a circuit of system 1600. The circuit includes a communicator 1711 and external neurostimulator 1710 coupled to stimulation electrodes 214 and sensor 322. Communicator 1711 includes user interface 328 and a communicator telemetry circuit 1794. External neurostimulator 1710 includes stimulation output circuit 216, stimulation controller 318, memory circuit 220, stimulator telemetry circuit 324, and battery 326. Communicator telemetry circuit 1794 and stimulator telemetry circuit 324 perform bi-directional communication between user interface 328 and stimulation controller 318 via telemetry link 1615. The circuit is substantially similar to the circuit in FIG. 3 except that user interface 328 is communicatively coupled to stimulation controller 318 via telemetry link 1615.

FIGS. 18-21 illustrate additional examples of stimulation electrodes coupled to external neurostimulator 410, including its various embodiments discussed in this document. In various embodiments, neurostimulation is delivered transcutaneously and/or percutaneously using one or more pairs of stimulation electrodes such as those illustrated in FIGS. 5-11 and 18-21, as well as any other suitable pairs of surface and/or percutaneous electrodes.

FIG. 18 is an illustration of another embodiment of surface stimulation electrodes coupled to external neurostimulator 410. Surface stimulation electrode 656A is connected to external neurostimulator 410 using lead 658A and is incorporated onto skin patch 659A, as discussed above with reference to FIG. 6. A surface stimulation electrode 1856B is incorporated onto the side of the chassis of external neurostimulator 410 that is in contact of the surface of body 102 when being used. One example of surface stimulation electrodes 1856B is surface stimulation electrode 556A/B as discussed above. The electrode configuration illustrated in FIG. 18 differs from the electrode configuration illustrated in FIG. 6 in that one of the surface electrodes is connected to external neurostimulator 410 using a lead, extending the range of stimulation targets with external neurostimulator 410 placed on a surface location of body 102. This provides for transcutaneous neurostimulation when, for example, it is difficult to place external neurostimulator 410 approximately over the stimulation target in body 102.

FIG. 19 is an illustration of an embodiment of surface and percutaneous stimulation electrodes coupled to external neurostimulator 410. Percutaneous stimulation electrode 756A is a wire electrode including a wire having a proximal end coupled to external neurostimulator 410 and a distal end configured to lodge in the specified stimulation site in body 102, as discussed above with reference to FIG. 7. A surface stimulation electrode 1956B is incorporated onto the side of the chassis of external neurostimulator 410 that is in contact of the surface of body 102 when being used. One example of surface stimulation electrodes 1956B is surface stimulation electrode 556A/B as discussed above. The electrode configuration illustrated in FIG. 19 differs from the electrode configuration illustrated in FIG. 7 in that one of the percutaneous electrodes is replaced by a surface electrode. This reduces the degree the invasiveness of the neurostimulation therapy.

FIG. 20 is an illustration of another embodiment of surface and percutaneous stimulation electrodes coupled to external neurostimulator 410. Percutaneous stimulation electrodes 856A is a wire electrode including a wire having a proximal end coupled to external neurostimulator 410 and a distal end configured to lodge in the specified stimulation site in body 102, as discussed above with reference to FIG. 8. A surface stimulation electrode 2056B is incorporated onto the side of the chassis of external neurostimulator 410 that is in contact of the surface of body 102 when being used. One example of surface stimulation electrodes 2056B is surface stimulation electrode 556A/B as discussed above. The electrode configuration illustrated in FIG. 20 differs from the electrode configuration illustrated in FIG. 8 in that one of the percutaneous electrodes is replaced by a surface electrode. This reduces the degree the invasiveness of the neurostimulation therapy.

FIG. 21 is an illustration of another embodiment of surface and percutaneous stimulation electrodes coupled to external neurostimulator 410. An implantable capsule 2162 includes a percutaneous stimulation electrodes 2156A on one of its opposite ends. To deliver the neurostimulation, capsule 2162 is subcutaneously implanted, and a lead 2158 provides a percutaneous connection between percutaneous stimulation electrode 2156A and external neurostimulator 410. Implantable capsule 2162 is substantially similar to implantable capsule 962 except that only one stimulation electrode is required to be incorporated onto the capsule. A surface stimulation electrode 2156B is incorporated onto the side of the chassis of external neurostimulator 410 that is in contact of the surface of body 102 when being used. One example of surface stimulation electrodes 2156B is surface stimulation electrode 556A/B as discussed above. The electrode configuration illustrated in FIG. 21 differs from the electrode configuration illustrated in FIG. 9 in that one of the stimulation electrodes is replaced by a surface electrode. This increases the distance between the pair of stimulation electrodes when needed.

Figure 22:
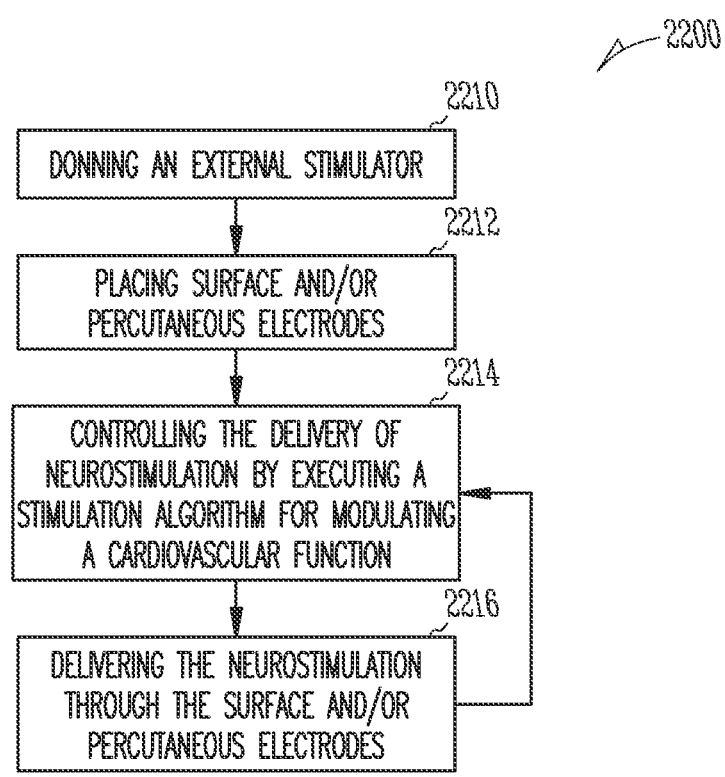
FIG. 22 is a flow chart illustrating a method for modulating a cardiovascular function using transcutaneous or percutaneous neurostimulation.

FIG. 22 is a flow chart illustrating a method 2200 for modulating a cardiovascular function using transcutaneous or percutaneous neurostimulation. In one embodiment, the method is performed by system 100, 1400, or 1600.

An external neurostimulator is donned onto a patient at 2210, upon determination that the patient is likely to benefit from a transcutaneous or percutaneous neurostimulation therapy. In one embodiment, the patient has suffered an acute MI. The external neurostimulator is held to a surface location of the patient's body using a bracing element such as a belt, a strap, or a sleeve that braces a portion of the body. In one embodiment, the transcutaneous or percutaneous neurostimulation therapy is applied when the patient is waiting to receive an implantable neurostimulator, when the use of an implantable neurostimulator is not justified, or when the use of an external neurostimulator is more beneficial to the patient when compared to the use of an implantable neurostimulator for medical, administrative, and/or economical reasons.

Surface and/or percutaneous electrodes are placed at 2212. Surface electrodes are used to deliver the transcutaneous neurostimulation therapy. Percutaneous and/or surface electrodes are used to deliver the percutaneous neurostimulation therapy. Examples of the surface and/or percutaneous electrodes include those illustrated in FIGS. 5-11 and 18-21, while all electrodes suitable for delivering transcutaneous or percutaneous neurostimulation therapy may be used. Factors determining the choice between the transcutaneous neurostimulation therapy and the percutaneous neurostimulation therapy include, for example, whether the patient or a trained medical personnel administers the therapy delivery, location of the intended stimulation target, device availability, and duration and/or frequency of the use of the neurostimulation device.

The delivery of the neurostimulation is controlled by executing a stimulation algorithm for modulating a cardiovascular function at 2214. In one embodiment, the execution of the stimulation algorithm is initiated by a neurostimulation command received from a user or another device. In one embodiment, the stimulation algorithm provides for an open-loop neurostimulation using predetermined stimulation parameters. In another embodiment, the stimulation algorithm provides for a closed-loop neurostimulation using a feedback control signal to adjust the stimulation parameters, including the starting and stopping of the delivery of the neurostimulation. In one embodiment, the feedback control signal is indicative of whether the neurostimulation elicits the intended response from the target nerve. Examples of the feedback control signal include a cardiac signal, a blood pressure signal, a plethysmographic signal, and any other signal indicative of cardiac functions and/or hemodynamic performance of the patient.

The neurostimulation is delivered through the surface and/or percutaneous electrodes at 2216. In one embodiment, the neurostimulation is a stand-alone therapy. In another embodiment, the neurostimulation is supplemental to a cardiac stimulation therapy such as a cardiac remodeling control therapy and/or other therapies such as drug and biologic therapies.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for transcutaneous neurostimulation to modulate a cardiovascular function in a body, the system comprising:
    a transcutaneous neurostimulation device configured to be worn on the body, the transcutaneous neurostimulation device including:
        surface stimulation electrodes configured to be placed on a surface of the body;
        an external neurostimulator configured to deliver neurostimulation transcutaneously to a stimulation target in the body through the surface stimulation electrodes, the external neurostimulator including:
            a stimulation output circuit electrically coupled to the surface stimulation electrodes and configured to deliver the neurostimulation through the surface stimulation electrodes;
            a memory circuit configured to store a history of the delivery of the neurostimulation by the external neurostimulator;
            a stimulation algorithm stored in the memory circuit, the stimulation algorithm including parameters selected to modulate the cardiovascular function;
            a stimulation controller coupled to the stimulation output circuit and the memory circuit and configured to control the delivery of the neurostimulation by executing the stimulation algorithm, the stimulation controller including a clock configured to start the delivery of the neurostimulation according to a programmed schedule; and
            a chassis housing at least the stimulation output circuit, the memory circuit, and the stimulation controller, wherein at least a first electrode of the surface stimulation electrodes is incorporated onto the chassis, and the neurostimulation is delivered through at least the first electrode; and
        a first bracing element coupled to the external neurostimulator, the first bracing element configured to brace a portion of the body to hold the external neurostimulator on a surface location of the body such that the first electrode is approximately on an acupuncture point, the first bracing element including a belt having an adjustable length or a sleeve having an adjustable length; and
    a portable user communication device suitable for being worn on a wrist of the body and including:
        a communicator communicatively coupled to the external neurostimulator via telemetry, the communicator including a user interface; and
        a second bracing element coupled to the communicator and configured to brace the wrist.

2. The system of claim 1, wherein the first bracing element is detachably coupled to the external neurostimulator.

3. The system of claim 1, wherein the stimulation controller comprises a feedback controller configured to control the delivery of the neurostimulation using a feedback control signal, and the external stimulator comprises an external sensor electrically coupled to the feedback controller and configured to sense the feedback control signal.

4. The system of claim 1, wherein the user interface comprises a user input device and a presentation device.

5. The system of claim 4, wherein the user input device comprises a power switch to turn the external neurostimulator on/off.

6. The system of claim 5, wherein the presentation device comprises a display configured to present one or more of an on/off status of the external neurostimulator, time, and battery status.

7. The system of claim 6, wherein the external neurostimulator comprises an external sensor configured to sense one or more of a heart rate and a blood pressure, and the display is further configured to present one or more of the heart rate and the blood pressure.

8. The system of claim 1, wherein the external neurostimulator comprises a rechargeable battery.

9. The system of claim 1, wherein the first bracing element is configured to brace the neck of the body.

10. The system of claim 1, wherein the first bracing element is in a form of a knee band or sleeve.

11. The system of claim 1, wherein the first bracing element is configured to brace a portion of the body to hold the external neurostimulator on the surface location of the body such that the first electrode is approximately on an acupuncture point at which electrical stimulation is known to have anti-remodeling and anti-arrhythmic effects.

12. The system of claim 11, wherein the first bracing element is configured to hold the first electrode approximately on the GB-34 acupuncture point of the Gall Bladder Meridian of the body.

13. The system of claim 1, wherein the stimulation controller comprises an alarm signal generator configured to generate an alarm signal as a reminder of the timed delivery of the neuro stimulation.

14. The system of claim 1, wherein the clock is configured to start the delivery of the neurostimulation according to a programmed periodic dose being a time interval during which the body is treated with the neurostimulation.

15. The system of claim 1, wherein the first bracing element is configured to hold the external neurostimulator on a knee area of the body.

16. The system of claim 1, wherein the first bracing element comprises a sleeve made of an elastic material to provide the adjustable length.

17. The system of claim 1, wherein the second bracing element comprises a sleeve made of an elastic material to provide the adjustable length.

* * * * *